United States Patent [19]

Buzzi et al.

[11] Patent Number: 4,922,936
[45] Date of Patent: May 8, 1990

[54] DENTAL CLEANER

[76] Inventors: Carlo A. Buzzi, Stauffacherstrasse 98, CH-8004 Zürich; Ulrich A. Saxer, Steinbrüchelstrasse 30, CH-8053 Zürich; Paul A. Stäger, Lindemstrasse 128, CH-8307 Effretikon, all of Switzerland

[21] Appl. No.: 187,522

[22] PCT Filed: Aug. 12, 1987

[86] PCT No.: PCT/CH87/00097
§ 371 Date: Apr. 11, 1988
§ 102(e) Date: Apr. 11, 1988

[87] PCT Pub. No.: WO88/01154
PCT Pub. Date: Feb. 25, 1988

[30] Foreign Application Priority Data

Aug. 14, 1986 [CH] Switzerland .......................... 3283/86

[51] Int. Cl.5 ............................................. A61C 15/00
[52] U.S. Cl. ..................................... 132/321; 132/329
[58] Field of Search ................. 132/89, 93, 321, 329

[56] References Cited

U.S. PATENT DOCUMENTS

| 792,471 | 6/1905 | Smith | 132/89 |
| 1,966,205 | 4/1935 | Jackson | 132/89 |
| 1,989,895 | 2/1935 | Gilder | 132/93 |
| 3,511,249 | 5/1970 | Baitz | 132/89 |
| 3,939,520 | 2/1976 | Axelsson | 132/93 |
| 4,265,258 | 5/1981 | Eaton | 132/89 |
| 4,538,315 | 9/1985 | Barth | 15/22 R |

FOREIGN PATENT DOCUMENTS

| 2925020 | 1/1981 | Fed. Rep. of Germany | 132/93 |
| 2220234 | 10/1974 | France | 132/93 |
| 2519543 | 7/1983 | France | 132/93 |
| 211202 | 11/1940 | Switzerland | 132/93 |
| 8201126 | 4/1982 | World Int. Prop. O. | 132/93 |

Primary Examiner—John J. Wilson
Attorney, Agent, or Firm—Bernard, Rothwell & Brown

[57] ABSTRACT

A dental cleaner in the nature of a toothpick has an elongated stable support which is covered with fine plastic flock particles of a small diameter in order to effectively clean small gaps between the teeth, between bridge anchors and in the sulcus region and to function as a type of "micro-bottle cleaner" for the spaces where plaque needs to be cleaned from the teeth.

11 Claims, 1 Drawing Sheet

DENTAL CLEANER

BACKGROUND OF THE INVENTION

This invention relates to improvements in dental cleaners in the nature of toothpicks.

BACKGROUND AND PRIOR ART

Toothpicks of various kinds have been proposed for cleaning teeth, in particular for cleaning the interdental embrasures. The conventional wood and quill toothpicks are used especially for removing residual food particles from the interdental embrasures. Greater effectiveness is achieved by those toothpicks, the wood of which swells under the action of dental saliva in the interdental embrasure, thereby completely filling the embrasure and at least partially detaching plaque deposits.

SUMMARY OF THE INVENTION

It has now been found that the effect of currently known toothpicks can be substantially increased if the latter are flocked. This enables the interdental embrasures to be brushed and thus cleaned by a type of "micro bottle cleaner" even in the concave interdental embrasure.

As compared with the conventional toothpicks, the novel dental cleaner has the advantage of cleaning much more effectively between the bridge anchors and in the sulcus region.

In addition, it can be made so thin that it can be pushed into even the narrowest embrasures to free these from plaque.

Suitable materials for the production of the new dental cleaner, for the support, are wood, bamboo and all physiologically acceptable plastics and metal having sufficient bending strength to push the cleaner into the interdental embrasures in spite of resistance. Plastics and metals can be cast to form a thin sheet and, after solidifying, stamped or processed to form round or angular wires. Among other things, supports made of glass- or carbon fibre-reinforced plastics may also be used. The support can be prepared by roughening or specific shaping such that better adhesion of the adhesive can be achieved for flocking. Shaping can further increase the effectiveness and stability of the toothpick if the plastic films or metal foils are, for example, deformed in the manner of a corrugated sheet. The direct application of the flock bristles to a heated plastic support, without adhesive, is the ideal, giving actual material bonding. In the case of plastic supports, excellent results are furthermore achieved if their surface is etched with a solvent and the thus treated surface is flocked. For certain support material, the use of an adhesive, e.g. araldite, is necessary for flocking.

Advantageously, the support has a length of 5 to 15 cm and the shape of a rod of, for example, round, triangular or polygonal, regular or irregular cross-section. The end to be introduced can be blunt or, preferably, tapered, solid or hollow. The flock coating can likewise be regular or irregular, total or partial stock.

Suitable materials for the bristles are primarily plastics which can be processed to give bristles of very small dimensions, e.g. nylon. Advantageously, the bristles have a length of about 0.3 to 0.8 mm, preferably about 0.5 mm and a diameter of about 1.7 to 5 dtex, preferably about 3.3 dtex, it being possible to apply bristles of various lengths and thicknesses to the same support. The materials can be colourless or dyed in bulk in any desired manner.

Flocking is carried out by known processes, as mentioned above, for example using a suitable physiologically acceptable adhesive or by flocking a still-tacky thermoplastic support surface or by flocking a plastic surface etched with a solvent.

The dental cleaner can be coated in flock of several colours, each colour indicating a different length of bristle. Colours can also indicate the diameter and type of toothpick or simply indicate a country or firm of origin. At the introduction end of the toothpick, the flock coating advantageously is tapered. It is also possible to flock the end with shorter bristles. The flocked toothpick can be provided with disinfectants, fluorides, flavourings or tooth-cleaning agents.

It goes without saying that the flocked toothpick is freed from poorly adhering bristles during manufacture, for example by means of air and brushes before it is sterilized and packed either individually or in a relatively large numbers and, if required, assembled to form a set of various sizes.

DETAILED DESCRIPTION OF THE PREFRRED EMBODIMENT

Figure 1:
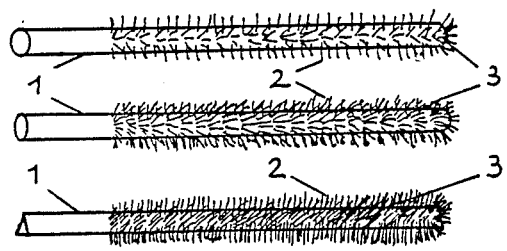
FIG. 1 represents a dental cleaner, the support of which has a round, oval or triangular cross-section and is flocked up to the introduction end.

In the drawing, the support is in each case indicated 1, the flock coating by 2 and the introduction end by 3.

Figure 2:
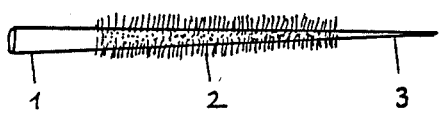
FIG. 2 shows a dental cleaner, the support of which is only partially flocked and tapers to a point at the introduction end.
Figure 3:
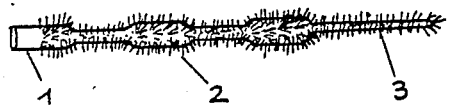
FIG. 3 shows a dental cleaner, the support of which changes in profile or diameter at intervals in order to achieve a type of sawtooth effect with bristles of equal length.

As can be seen from FIGS. 1 to 3, the flock coating can cover either the entire surface of the support or only part of it, e.g. can leave the introduction end uncovered or be arranged in the form of a spiral or in any desired pattern. It is, for example, possible to apply trademarks or letters etc. by means of the flock coating. However, it is likewise also possible to indicate differences in the length and/or thickness of the bristles by the choice of various bristle colours.

Figure 4:
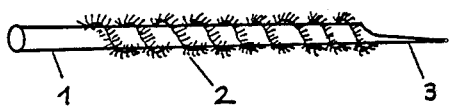
FIG. 4 shows a dental cleaner, the flock coating of which has been applied in a spiral.

In FIG. 1, the introduction end is blunt, in FIG. 2 pointed and in FIG. 4 quill-shaped. In the case of narrow interdental embrasures, the use of a pointed or quill-shaped introduction end is to be recommended.

Figure 5:
FIG. 5 shows an embodiment in which the wire-shaped, flocked support is accommodated in a tube-shaped sheath from which it can be pushed out and fixed at any desired length.

FIG. 5 shows an embodiment with a wire-shaped support of about 0.3 mm diameter of metal, carbon-reinforced or glass fiber-reinforced plastic, which is uniformly flocked over a length of about 5 cm. At its rear end, the support is attached to the holder 4 and pushed into the plastic sheath 6. By means of the cam 5, which is moved in a longitudinal groove in the sheath and can be locked at various points by a slight turn into a recess (not shown), the cleaner can either be retracted completely into the sheath or fixed at the desired depth.

It is obvious to the person skilled in the art that numerous further embodiments and materials are possible for the support, the bristles and the arrangement.

We claim:

1. A method of making a dental cleaner in the nature of a toothpick in which an elongated rigid support is at least partially covered with bristles, the method comprising,
   providing a rigid stable support, and
   placing plastic bristles which are in the nature of flock on the support by flocking.

2. The method of claim 1 wherein the step of providing a rigid stable support further comprises providing said support with a tapered end to be introduced in an interdental embrasure, and wherein bristles are placed on the tapered end by flocking.

3. The method of claim 1 wherein when said plastic bristles are placed on said rigid stable support, one end of the support is not flocked.

4. The method of claim 1 wherein the step of providing a rigid stable support further comprises providing said rigid support preshaped with variations in cross sections of said support, and wherein plastic bristles of equal length are placed on said support so that the plastic bristles of equal length provide a saw-tooth effect due to variations in the cross sections of said support.

5. The method of claim 1 further comprising the step of providing at least some of the bristles with a cleaning agent.

6. The method of claim 1 wherein the step of providing a rigid stable support further comprises forming said support of plastic material.

7. The method of claim 6 further including the step of providing said plastic material with reinforcement selected from the group consisting of carbon fiber and glass fiber.

8. The method of claim 1 wherein said plastic bristles are placed on said support so that said support is flocked in a tapering manner.

9. The method of claim 1 further including the step of providing said bristles with a disinfecting agent.

10. The method of claim 1 wherein said flocking comprises electrostatic flocking.

11. The method of claim 1 wherein the step of placing said plastic bristles on said support comprises placing plastic bristles having a diameter of between 1.7 and 5 dtex on said support.

* * * * *

REEXAMINATION CERTIFICATE (3780th)

United States Patent [19]
Buzzi et al.

[11] B1 4,922,936
[45] Certificate Issued Jun. 8, 1999

[54] DENTAL CLEANER

[75] Inventors: Carlo A. Buzzi; Ulrich A. Saxer, both of Zürich; Paul A. Stäger, Effretikon, all of Switzerland

[73] Assignees: Ulrich Peter Saxer, Zurich; Walter Koller, Waldkirch; Franz Aschwanden, Gersau, all of Switzerland

Reexamination Request:
No. 90/004,820, Oct. 29, 1997

Reexamination Certificate for:
Patent No.: 4,922,936
Issued: May 8, 1990
Appl. No.: 07/187,522
Filed: Apr. 11, 1988

[21] Appl. No.: 07/187,522
[22] PCT Filed: Aug. 12, 1987
[86] PCT No.: PCT/CH87/00097
    § 371 Date: Apr. 11, 1988
    § 102(e) Date: Apr. 11, 1988
[87] PCT Pub. No.: WO88/01154
    PCT Pub. Date: Feb. 25, 1988

[30] Foreign Application Priority Data
Aug. 14, 1986 [CH] Switzerland ............... 3283/86

[51] Int. Cl.⁶ ..................................................... A61C 15/00
[52] U.S. Cl. ................................................. 132/321; 132/329
[58] Field of Search ................................. 132/321, 329, 132/309, 323

[56] References Cited

U.S. PATENT DOCUMENTS

| | | | |
|---|---|---|---|
| 792,471 | 6/1905 | Smith | 132/329 |
| 1,989,895 | 2/1935 | Van Gilder | 132/323 |
| 1,996,205 | 4/1935 | Jackson | 132/309 |
| 3,511,249 | 5/1970 | Baitz | 132/329 |
| 3,698,405 | 10/1972 | Walker | 132/309 |
| 3,939,520 | 2/1976 | Axelsson | 132/308 |
| 4,265,258 | 5/1981 | Eaton | 132/321 |
| 4,538,315 | 9/1985 | Barth | 15/23 |
| 4,687,257 | 8/1987 | Stern | 300/21 |
| 4,830,032 | 5/1989 | Jousson | 132/323 |

FOREIGN PATENT DOCUMENTS

| | | |
|---|---|---|
| 2220234 | 10/1974 | France. |
| 2519543 | 7/1983 | France. |
| 2925020 | 1/1981 | Germany. |
| 211202 | 11/1940 | Switzerland. |
| 8201126 | 4/1982 | WIPO. |

*Primary Examiner*—John J. Wilson

[57] ABSTRACT

A dental cleaner in the nature of a toothpick has an elongated stable support which is covered with fine plastic flock particles of a small diameter in order to effectively clean small gaps between the teeth, between bridge anchors and in the sulcus region and to function as a type of "micro-bottle cleaner" for the spaces where plaque needs to be cleaned from the teeth.

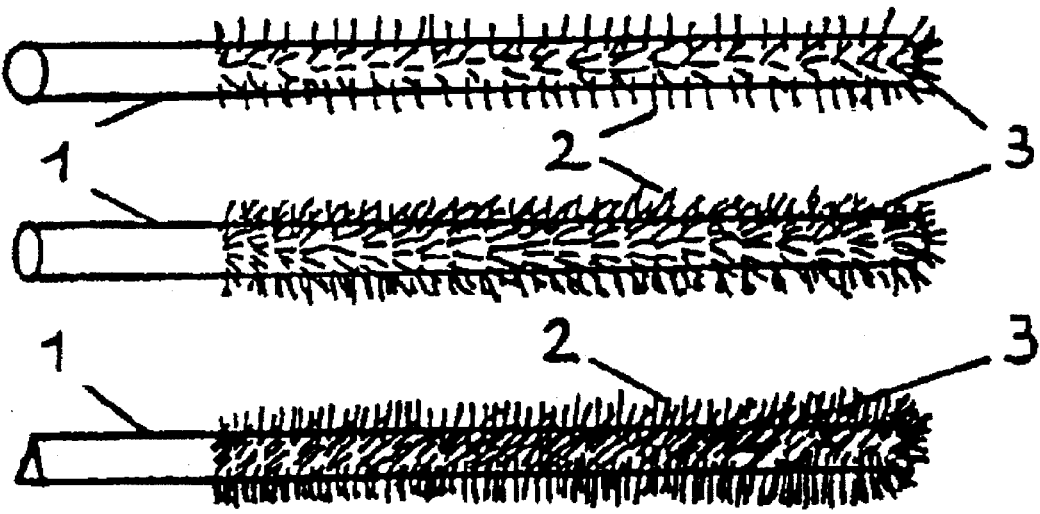

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-11 having been finally determined to be unpatentable, are cancelled.

* * * * *